(12) United States Patent
Moffitt et al.

(10) Patent No.: US 10,369,364 B2
(45) Date of Patent: *Aug. 6, 2019

(54) DEVICES AND METHODS TO USE POWER SPECTRUM OR SIGNAL ASSOCIATION FOR PAIN MANAGEMENT

(71) Applicant: Boston Scientific Neuromodulation Corporation, Valencia, CA (US)

(72) Inventors: Michael A. Moffitt, Saugus, CA (US); Hemant Bokil, Santa Monica, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/138,381

(22) Filed: Sep. 21, 2018

(65) Prior Publication Data

US 2019/0022395 A1   Jan. 24, 2019

Related U.S. Application Data

(63) Continuation of application No. 15/890,008, filed on Feb. 6, 2018, now Pat. No. 10,130,816, which is a (Continued)

(51) Int. Cl.
*A61B 5/00* (2006.01)
*A61N 1/36* (2006.01)
(Continued)

(52) U.S. Cl.
CPC .......... *A61N 1/36071* (2013.01); *A61B 5/048* (2013.01); *A61B 5/0476* (2013.01); (Continued)

(58) Field of Classification Search
CPC ................. A61N 1/36071; A61N 1/36139
(Continued)

(56) References Cited

U.S. PATENT DOCUMENTS 4,813,418 A    3/1989  Harris
6,067,474 A    5/2000  Schulman et al.
(Continued)

FOREIGN PATENT DOCUMENTS

DE      10318071 A1    11/2004
WO      02/09808 A1     2/2002
WO   2009/055127 A1     4/2009

OTHER PUBLICATIONS

Larson, J. et al., "Reversal of LTP by theta frequency stimulation", Brain Research, Elsevier, Amsterdam, NL, vol. 600 No. 1, Jan. 8, 1993, pp. 97-102.

(Continued)

*Primary Examiner* — Nadia A Mahmood
(74) *Attorney, Agent, or Firm* — Lowe Graham Jones PLLC; Bruce E. Black

(57) ABSTRACT

Methods and systems for electrical stimulation can include obtaining a biosignal of the patient; altering at least one stimulation parameter of an electrical stimulation system in response to the biosignal; and delivering an electrical stimulation current to one or more selected electrodes of the electrical stimulation system using the at least one stimulation parameter. In some embodiments, a power spectrum is determined from the biosignal. In some embodiments, the biosignal is at least two different biosignals measured at the same or different locations on the patient and a coherence, correlation, or association between the two biosignal is determined.

20 Claims, 9 Drawing Sheets

Related U.S. Application Data continuation of application No. 14/861,524, filed on Sep. 22, 2015, now Pat. No. 9,925,378.

(60) Provisional application No. 62/053,427, filed on Sep. 22, 2014.

(51) Int. Cl.
*A61B 5/0476* (2006.01)
*A61B 5/048* (2006.01)

(52) U.S. Cl.
CPC ........ *A61N 1/36139* (2013.01); *A61B 5/7246* (2013.01); *A61B 5/7257* (2013.01)

(58) Field of Classification Search
USPC ...................................... 607/45, 46
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,917,221 B2 | 3/2011 | Tass |
| 7,949,395 B2 | 5/2011 | Kuzma |
| 7,974,698 B2 | 7/2011 | Tass et al. |
| 7,974,706 B2 | 7/2011 | Moffitt et al. |
| 8,000,794 B2 | 8/2011 | Lozano |
| 8,000,795 B2 | 8/2011 | Lozano |
| 8,000,796 B2 | 8/2011 | Tass et al. |
| 8,078,275 B2 | 12/2011 | Lozano |
| 8,116,874 B2 | 2/2012 | Tass |
| 8,175,710 B2 | 5/2012 | He |
| 8,224,450 B2 | 7/2012 | Brase |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,346,365 B2 | 1/2013 | Lozano |
| 8,364,278 B2 | 1/2013 | Pianca et al. |
| 8,380,304 B2 | 2/2013 | Lozano |
| 8,391,985 B2 | 3/2013 | McDonald |
| 8,463,378 B2 | 6/2013 | Tass |
| 8,463,386 B2 | 6/2013 | Tass |
| 8,538,547 B2 | 9/2013 | Tass et al. |
| 8,565,883 B2 | 10/2013 | Lozano |
| 8,612,006 B2 | 12/2013 | Lozano et al. |
| 8,868,191 B2 | 10/2014 | Lozano |
| 9,227,066 B2 | 1/2016 | Lozano |
| 2003/0191506 A1 | 10/2003 | Shloznikov |
| 2004/0210271 A1 | 10/2004 | Campen |
| 2005/0075696 A1 | 4/2005 | Forsberg et al. |
| 2005/0216071 A1 | 9/2005 | Devlin et al. |
| 2006/0015153 A1 | 1/2006 | Bradford et al. |
| 2006/0212090 A1 | 9/2006 | Lozano et al. |
| 2007/0142874 A1 | 6/2007 | John |
| 2007/0150036 A1 | 6/2007 | Anderson |
| 2007/0225674 A1 | 9/2007 | Molnar et al. |
| 2008/0071325 A1 | 3/2008 | Bradley |
| 2008/0215113 A1 | 9/2008 | Pawlowicz |
| 2009/0082829 A1 | 3/2009 | Panken et al. |
| 2009/0112281 A1 | 4/2009 | Miyazawa et al. |
| 2009/0187222 A1 | 7/2009 | Barker |
| 2009/0276021 A1 | 11/2009 | Meadows et al. |
| 2009/0281594 A1 | 11/2009 | King et al. |
| 2010/0268298 A1 | 3/2010 | Pianca et al. |
| 2010/0076535 A1 | 5/2010 | Pianca et al. |
| 2011/0004267 A1 | 1/2011 | Meadows et al. |
| 2011/0077720 A1 | 3/2011 | Torgerson et al. |
| 2011/0078900 A1 | 4/2011 | Pianca et al. |
| 2011/0130817 A1 | 6/2011 | Chen |
| 2011/0130818 A1 | 6/2011 | Chen |
| 2011/0201977 A1 | 8/2011 | Tass |
| 2011/0238129 A1 | 9/2011 | Moffitt et al. |
| 2011/0251583 A1 | 10/2011 | Miyazawa et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0274273 A1 | 11/2012 | Jacobs et al. |
| 2012/0316615 A1 | 12/2012 | DiGiore et al. |
| 2013/0066394 A1 | 3/2013 | Saab |
| 2013/0105071 A1 | 5/2013 | DiGiore et al. |
| 2013/0218239 A1 | 8/2013 | Grill et al. |
| 2013/0231713 A1 | 9/2013 | De Ridder |
| 2013/0289385 A1 | 10/2013 | Lozano et al. |
| 2013/0317583 A1 | 11/2013 | Pianca |
| 2013/0317585 A1 | 11/2013 | Barker |
| 2013/0317586 A1 | 11/2013 | Pianca |
| 2013/0317587 A1 | 11/2013 | Barker |
| 2013/0317588 A1 | 11/2013 | Howard et al. |
| 2014/0025133 A1 | 1/2014 | Lozano |
| 2014/0081349 A1 | 3/2014 | Lee et al. |
| 2014/0277250 A1 | 9/2014 | Su et al. |
| 2014/0277281 A1 | 9/2014 | Grandhe |
| 2016/0030666 A1 | 2/2016 | Lozano et al. |

OTHER PUBLICATIONS

International Search Report and Written Opinion for Application PCT/US2015/051460 dated Dec. 18, 2015, 14 pages.

Official Communication for U.S. Appl. No. 14/861,524 dated Nov. 8, 2016.

Official Communication for U.S. Appl. No. 14/861,524 dated May 16, 2017.

Official Communication for U.S. Appl. No. 15/890,008 dated Apr. 11, 2018.

DEVICES AND METHODS TO USE POWER SPECTRUM OR SIGNAL ASSOCIATION FOR PAIN MANAGEMENT

CROSS-REFERENCE TO RELATED APPLICATIONS

This application is a continuation of U.S. patent application Ser. No. 15/890,008, filed Feb. 6, 2018, which is a continuation of U.S. patent application Ser. No. 14/861,524, filed Sep. 22, 2015, which issued as U.S. Pat. No. 9,925,378, and which claims the benefit under 35 U.S.C. § 119(e) of U.S. Provisional Patent Application Ser. No. 62/053,427, filed Sep. 22, 2014, all of which are incorporated herein by reference.

FIELD

The present invention is directed to the area of implantable electrical stimulation systems and methods of making and using the systems. The present invention is also directed to implantable electrical stimulation systems that use a measured power spectrum or signal coherence or other measure of association to modify or alter stimulation parameters, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a non-transitory computer-readable medium having processor-executable instructions for adjusting stimulation parameters of an electrical stimulation system including a control module implanted in a patient, the processor-executable instructions when installed onto a device enable the device to perform actions. The actions include obtaining a biosignal of the patient; and altering at least one stimulation parameter of an electrical stimulation system in response to the biosignal.

In at least some embodiments, the actions further include delivering an electrical stimulation current to one or more selected electrodes of the electrical stimulation system using the at least one stimulation parameter. In at least some embodiments, the actions further include communicating the at least one stimulation parameter to an implantable control module. In at least some embodiments, the actions further include determining a power spectrum from the biosignal, where altering at least one stimulation parameter includes altering at least one stimulation parameter of the electrical stimulation system in response to the power spectrum. In at least some embodiments, the actions further include repeating the obtaining, altering and delivering actions at least once.

In at least some embodiments, the biosignal is at least two different biosignals and the actions further include determining a coherence, correlation, or association between the at least two different biosignals, where altering at least one stimulation parameter includes altering at least one stimulation parameter of the electrical stimulation system in response to the coherence, correlation, or association between the at least two different biosignals.

In at least some embodiments, the biosignal includes at least one band of an electroencephalograph of the patient. In at least some embodiments, the at least one band is a theta band.

Another embodiment is an electrical stimulation system that includes an implantable control module for implantation in a body of a patient and having an antenna and a processor coupled to the antenna. The control module is configured and arranged to provide electrical stimulation signals to an electrical stimulation lead coupled to the implantable control module for stimulation of patient tissue. The system also includes an external programming unit configured and arranged to communicate with the processor of the implantable control module using the antenna and to adjust stimulation parameters for production of the electrical stimulation signals. The external programming unit includes a user interface configured and arranged to receive input from a user, and a processor in communication with the user interface and configured and arranged to perform the following actions: obtaining a biosignal of the patient; altering at least one stimulation parameter of an electrical stimulation system in response to the biosignal; and communicating the at least one stimulation parameter to the implantable control module.

Yet another embodiment is an electrical stimulation system including an implantable control module configured and arranged for implantation in a body of a patient. The control module is configured and arranged to provide electrical stimulation signals to an electrical stimulation lead coupled to the implantable control module for stimulation of patient tissue. The implantable control module includes an antenna configured and arranged to receive input, and a processor in communication with the antenna and configured and arranged to perform the following actions: obtaining a biosignal of the patient via the antenna; altering at least one stimulation parameter of an electrical stimulation system in response to the biosignal; and delivering an electrical stimulation current to one or more selected electrodes of the electrical stimulation system using that at least one stimulation parameter.

In at least some embodiments, any of the systems can include at least one sensor configured and arranged to obtain the biosignal of the patient. In at least some embodiments, in any of the systems the actions further include determining a power spectrum from the biosignal, where altering at least one stimulation parameter comprises altering at least one stimulation parameter of the electrical stimulation system in response to the power spectrum. In at least some embodiments, in any of the systems the biosignal is at least two different biosignals and the actions further include determining a coherence, correlation, or association between the at least two different biosignals, where altering at least one stimulation parameter comprises altering at least one stimulation parameter of the electrical stimulation system in response to the coherence, correlation, or association between the at least two different biosignals.

In at least some embodiments, any of the systems can include an electrical stimulation lead coupleable to the implantable control module and comprising a plurality of electrodes disposed along a distal end portion of the electrical stimulation lead. In at least some embodiments, in any of the systems the biosignal is at least one band of an electroencephalograph of the patient, wherein the at least one band is a theta band.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that use a measured power spectrum or signal coherence or other measure of association to modify or alter stimulation parameters, as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
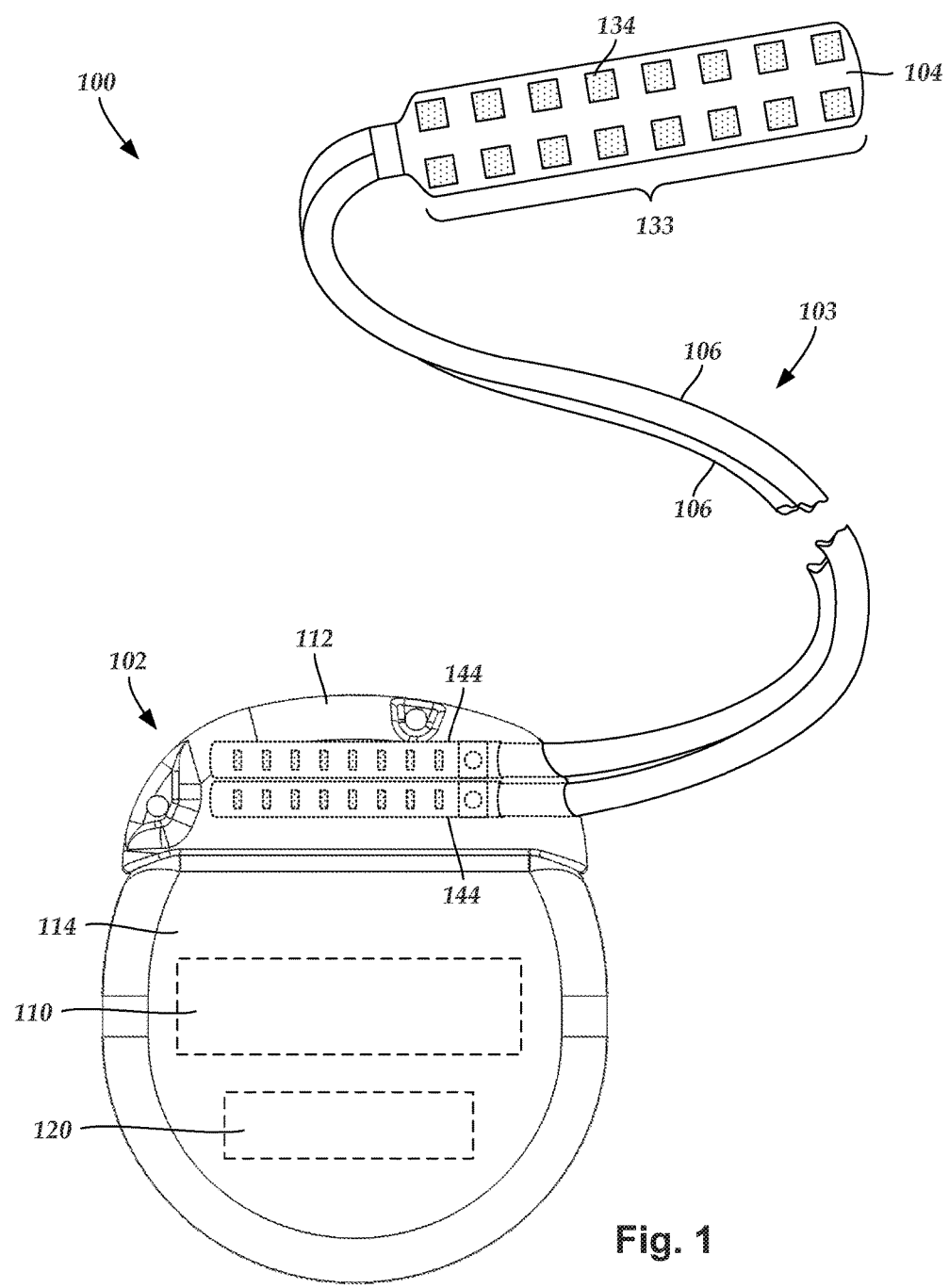
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
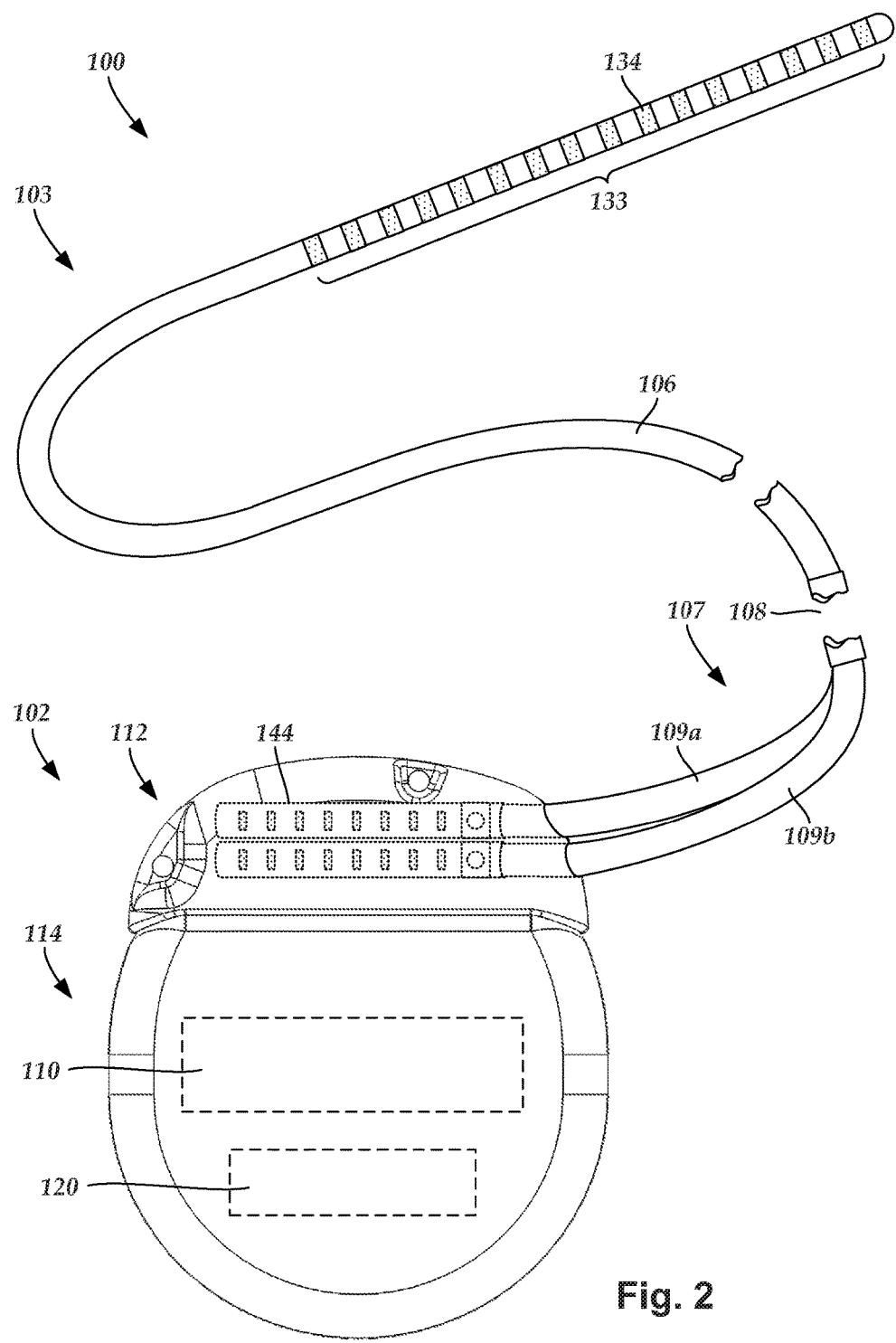
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
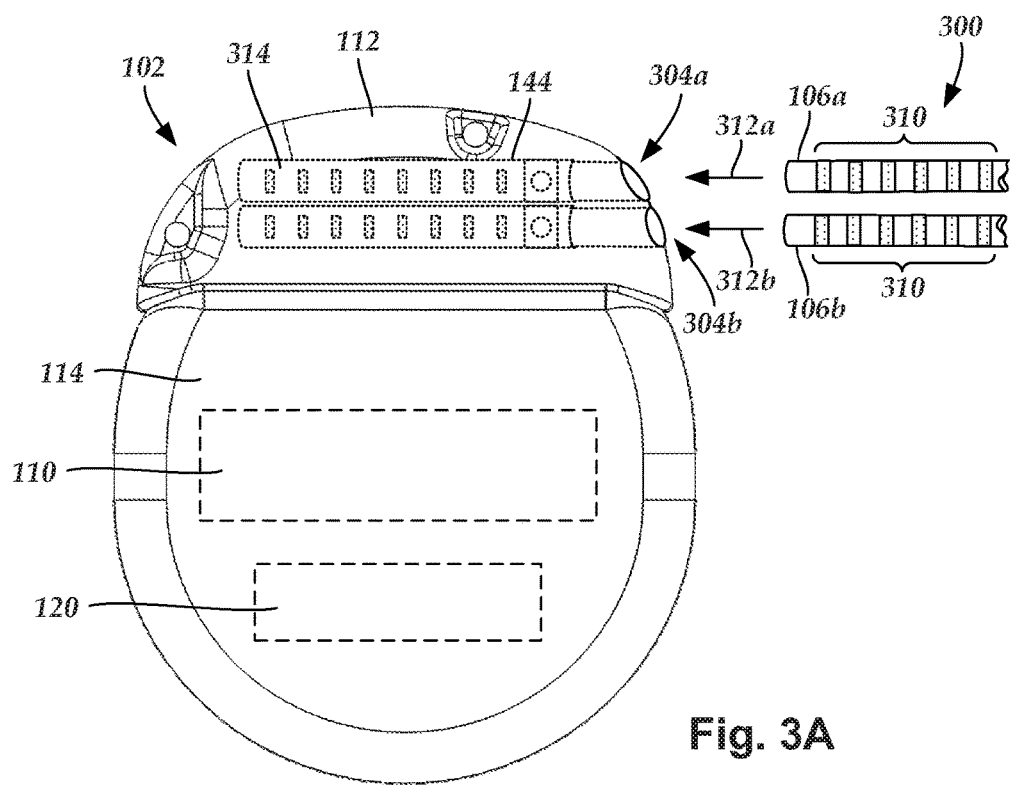
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
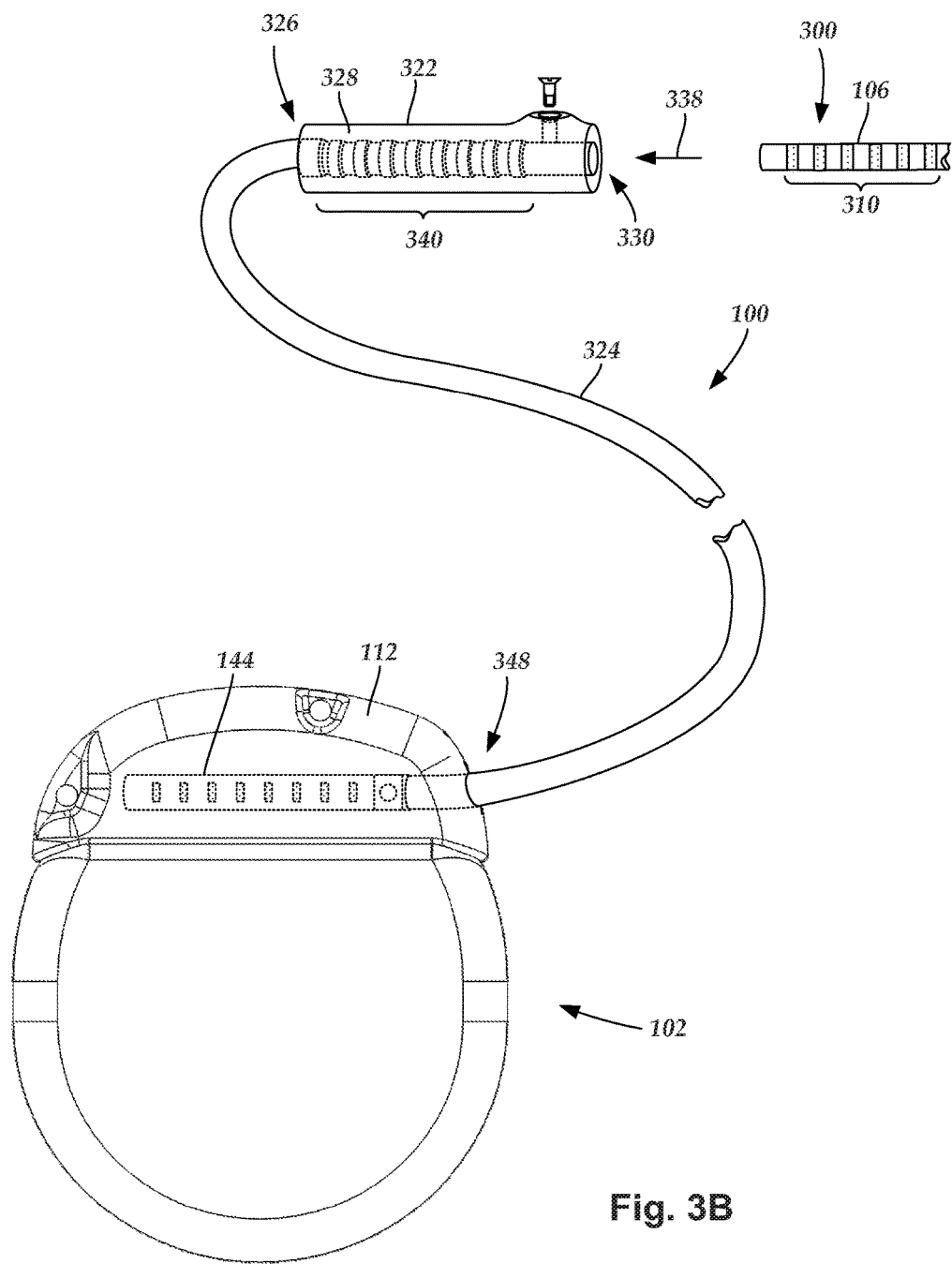
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

It is known that brain waves and other waves can adopt oscillatory patterns within a number of different frequency bands. For example, brain wave bands have been detected as biosignals using EEG and other methods and have been designated as, for example, delta, theta, alpha, beta, and gamma bands and the like. It at least some instances particular frequencies or frequency ranges within these bands can be indicative of abnormal conditions. As an example, it has been found that pain signals can be associated with frequencies in the theta band (approximately 4-8 Hz) that are shifted in frequency from a normal, "pain-free" frequency or frequency range within that band.

Although not wishing to be bound by any particular theory, it is thought that observing one or more of these frequency bands or portions of the frequency bands can indicate efficacy of treatment and can be used to adjust stimulation parameters. Other biosignals can also be observed and used to adjust stimulation parameters. In at least some embodiments, the power spectrum of a biosignal can be determined and used to adjust stimulation parameters. The power spectrum displays signal power as a function of frequency. The determination of a power spectrum from a time-varying signal, such as a biosignal, is well known and can include, for example, Fourier transformation of the biosignal or the like. In at least some embodiments, the theta band (4-8 Hz) or a portion of the theta band is observed and a power spectrum is calculated. One or more stimulation parameters can then be adjusted based on the power spectrum to enhance or improve the efficacy of the electrical stimulation.

Additionally or alternatively, two different biosignals can be measured and the coherence, correlation, or any other measure of association between the two biosignals can be determined. The two different biosignals can be, for example, the same type of biosignal measured at two different locations on the patient's body or two different types of biosignals measured at the same or different locations on the patient's body. As one example of the latter case, the two different types of biosignals can be 1) an EEG of the theta band and 2) an EEG of the gamma band. It will also be understood that more than two biosignals (for example, three, four, or more biosignals) can be measured and the coherence, correlation, or any other measure of association between the biosignals can be determined. Other measures of association can include, but are not limited to, power spectrum (a spectrum is a Fourier transform of the autocorrelation and can be a measure of association of a signal at one time point with the same signal at another time point), phase-amplitude coupling, bicoherence, or the like.

The existence of coherence, correlation, or other association between two or more different biosignals can be indicative of synchronous activity which can be indicative or pain or other abnormal condition that is transmitted along the neural tissue. The determination of coherence, correlation, or association between two or more signals is well-known and can be implemented for the biosignals. In at least some embodiments, the theta band (4-8 Hz) or a portion of the theta band is observed at two different locations and coherence, correlation, or association between the two or more biosignals is calculated. In at least some embodiments, the theta band (4-8 Hz) or the gamma band (25-90 Hz) may be acquired at the same location or different locations and coherence or correlation or other measure of association between the two biosignals is calculated. One or more stimulation parameters can then be adjusted based on the coherence, correlation, or association to enhance or improve the efficacy of the electrical stimulation. Additional examples of stimulation at two different stimulation sites to desynchronize synchronous activity can be found in U.S. Provisional Patent Application Ser. No. 62/053,589, filed on even date herewith.

In at least some embodiments, the determination of either the power spectrum of a biosignal or the association (e.g., coherence, correlation, or the like) between two or more biosignals followed by the adjustment of stimulation parameters can be used in a feedback loop during a system programming session to select final stimulation parameters. For example, an external programming unit can provide stimulation parameters to a control module which generates the electrical stimulation. One or more sensors can then be used to obtain the biosignal(s) and the power spectrum or association (e.g., coherence, correlation, or the like) can then be determined. This information can be provided to a user or to the external programming unit and the stimulation parameters can be adjusted manually or automatically in response.

In at least some embodiments, the determination of either the power spectrum of a biosignal or the association (e.g., coherence, correlation, or the like) between two or more biosignals followed by the adjustment of stimulation parameters and the adjustment of stimulation parameters can be used in a feedback loop during system operation to adjust stimulation parameters to improve the efficacy of stimulation. For example, a control module generates the electrical stimulation using a set of stimulation parameters. One or more sensors can then be used to obtain the biosignal(s) and the power spectrum or association (e.g., coherence, correlation, or the like) can then be determined. This information can be provided to the control module (optionally, the control module can determine the power spectrum or association (e.g., coherence, correlation, or the like) using the biosignal(s) from the sensor(s)) and the stimulation parameters can be adjusted automatically in response.

Figure 4:
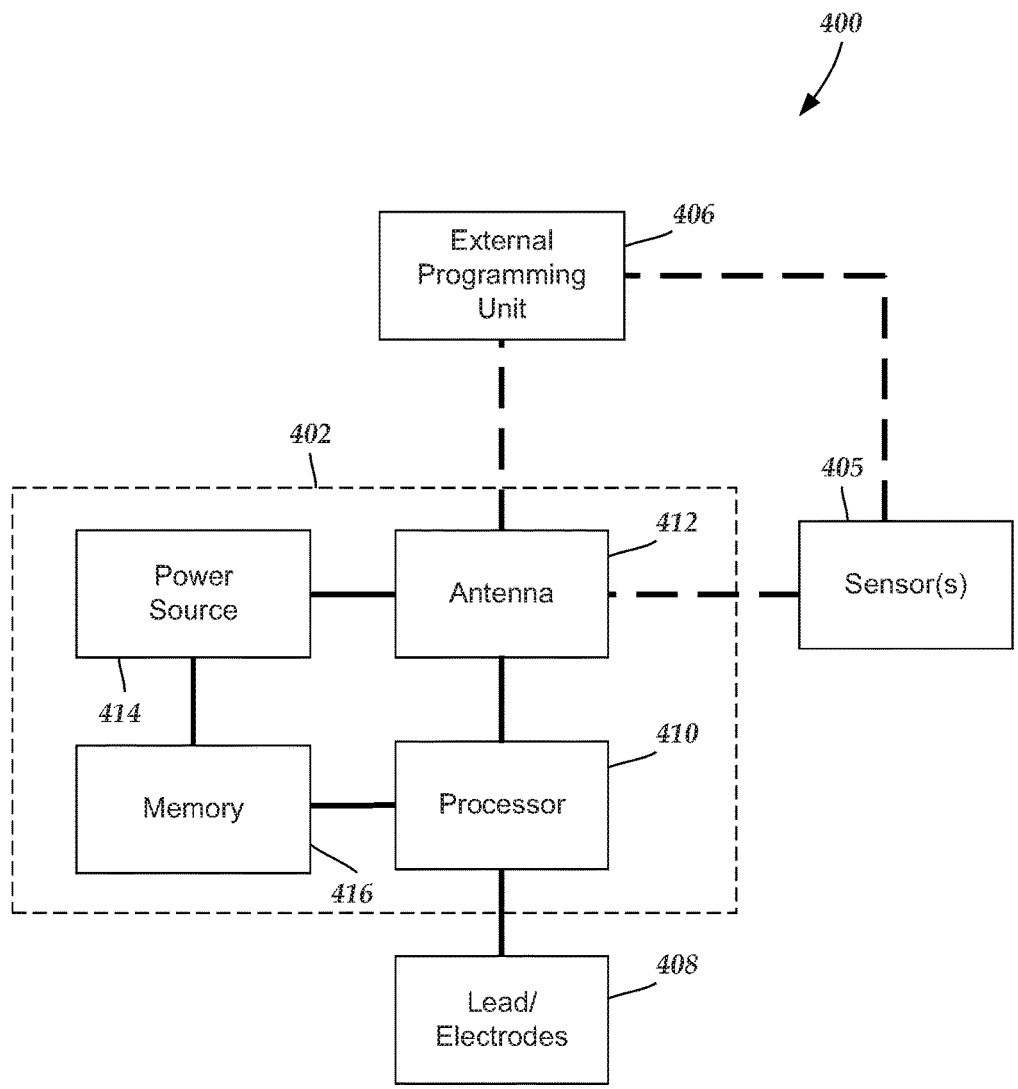
FIG. 4 is a schematic block diagram of one embodiment of an electrical stimulation system, according to the invention.

An electrical stimulation system includes a stimulator (for example, a control module/lead or a microstimulator). Any suitable stimulation system can be used including those described in the reference cited above. FIG. 4 illustrates schematically one embodiment of an electrical stimulation system 400 that includes an implantable control module (e.g., an implantable electrical stimulator or implantable pulse generator) 402, one or more leads 408 with electrodes, one or more external programming units 406, and one or more sensors 405. Alternatively, the implantable control module 402 can be part of a microstimulator with the electrodes disposed on the housing of the microstimulator. The microstimulator may not include a lead or, in other embodiments, a lead may extend from the microstimulator. It will be understood that the electrical stimulation system can include more, fewer, or different components and can have a variety of different configurations including those configurations disclosed in the references cited herein.

The lead 408 is coupled, or coupleable, to the implantable control module 402. The implantable control module 402 includes a processor 410, an antenna 412 (or other communications arrangement), a power source 414, and a memory 416, as illustrated in FIG. 4.

Figure 5:
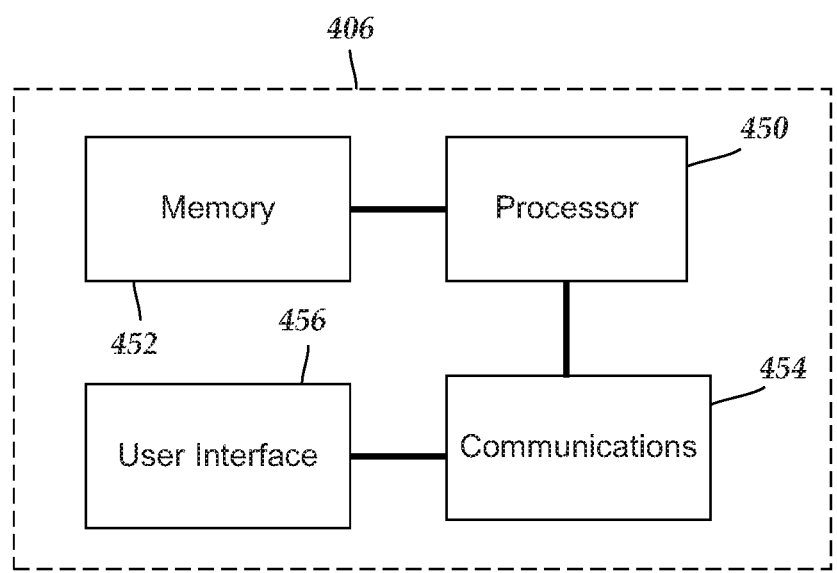
FIG. 5 is a schematic block diagram of one embodiment of an external programming unit, according to the invention.

An external programming unit 406 can include, for example, a processor 450, a memory 452, a communications arrangement 454 (such as an antenna or any other suitable communications device such as those described below), and a user interface 456, as illustrated in FIG. 5. Suitable devices for use as an external programming unit can include, but are not limited to, a computer, a tablet, a mobile telephone, a personal desk assistant, a dedicated device for external programming, remote control, or the like. It will be understood that the external programming unit 406 can include a power supply or receive power from an external source or any combination thereof. In at least some embodiments, the external programming unit 406 may also be a patient interface unit.

The one or more sensors 405 can be any suitable sensors for measuring a biosignal. Examples of biosignals include EEG, electrocochleograph (ECOG), heart rate, ECG, blood pressure, electrical signals traversing the spinal cord or a nerve or group of nerves, and the like. Any sensor suitable for measuring the corresponding biosignal can be used. The sensor can be implanted or positioned on the body of the patient. In some embodiments, at least one sensor is provided on the lead and can be, for example, a separate recording electrode for recording electrical signals or can be one or more stimulating electrodes that also are used for recording electrical signals. The sensor 405 can be in communication with the external programming unit 406 of the control module 402 or both. Such communication can be wired or wireless or any combination thereof using any of the methods described below. In at least some embodiments, the sensor 405 is deployed and used only during a programming session. In other embodiments, the sensor 405 may be deployed on or within the patient and in regular or constant communication with the control module 402.

Methods of communication between devices or components of a system can include wired or wireless (e.g., RF, optical, infrared, near field communication (NFC), Bluetooth™, or the like) communications methods or any combination thereof. By way of further example, communication methods can be performed using any type of communication media or any combination of communication media including, but not limited to, wired media such as twisted pair, coaxial cable, fiber optics, wave guides, and other wired media and wireless media such as acoustic, RF, optical, infrared, NFC, Bluetooth™ and other wireless media. These communication media can be used for communications arrangements in the external programming unit 406 or in the sensor 405 or as antenna 412 or as an alternative or supplement to antenna 412.

Turning to the control module 402, some of the components (for example, a power source 414, an antenna 412, and a processor 410) of the electrical stimulation system can be positioned on one or more circuit boards or similar carriers within a sealed housing of the control module (implantable pulse generator,) if desired. Any power source 414 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the antenna 412 or a secondary antenna. The external power source can be in a device that is mounted on the skin of the user or in a unit that is provided near the user on a permanent or periodic basis.

If the power source 414 is a rechargeable battery, the battery may be recharged using the antenna 412, if desired. Power can be provided to the battery for recharging by inductively coupling the battery through the antenna to a recharging unit external to the user.

A stimulation signal, such as electrical current in the form of electrical pulses, is emitted by the electrodes of the lead 408 (or a microstimulator) to stimulate neurons, nerve fibers, muscle fibers, or other body tissues near the electrical stimulation system. Examples of leads are described in more detail below. The processor 410 is generally included to control the timing and electrical characteristics of the electrical stimulation system. For example, the processor 410 can, if desired, control one or more of the timing, frequency, strength, duration, and waveform of the pulses. In addition, the processor 410 can select which electrodes can be used to provide stimulation, if desired. In some embodiments, the processor 410 selects which electrode(s) are cathodes and which electrode(s) are anodes. In some embodiments, the processor 410 is used to identify which electrodes provide the most useful stimulation of the desired tissue.

With respect to the control module 402 and external programming unit 406, any suitable processor 410, 450 can be used in these devices. For the control module 402, the processor 410 is capable of receiving and interpreting instructions from an external programming unit 406 that, for example, allows modification of pulse characteristics. In the illustrated embodiment, the processor 410 is coupled to the antenna 412. This allows the processor 410 to receive instructions from the external programming unit 406 to, for example, direct the pulse characteristics and the selection of electrodes, if desired. The antenna 412, or any other antenna described herein, can have any suitable configuration including, but not limited to, a coil, looped, or loopless configuration, or the like.

In one embodiment, the antenna 412 is capable of receiving signals (e.g., RF signals) from the external programming unit 406. The external programming unit 406 can be a home station or unit at a clinician's office or any other suitable device. In some embodiments, the external programming unit 406 can be a device that is worn on the skin of the user or can be carried by the user and can have a form similar to a pager, cellular phone, or remote control, if desired. The external programming unit 406 can be any unit that can provide information to the control module 402. One example of a suitable external programming unit 406 is a computer operated by the user or clinician to send signals to the control module 402. Another example is a mobile device or an application on a mobile device that can send signals to the control module 402

The signals sent to the processor 410 via the antenna 412 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the control module 402 to cease operation, to start operation, to start charging the battery, or to stop charging the battery.

Optionally, the control module 402 may include a transmitter (not shown) coupled to the processor 410 and the antenna 412 for transmitting signals back to the external programming unit 406 or another unit capable of receiving the signals. For example, the control module 402 may transmit signals indicating whether the control module 402 is operating properly or not or indicating when the battery needs to be charged or the level of charge remaining in the battery. The processor 410 may also be capable of transmitting information about the pulse characteristics so that a user or clinician can determine or verify the characteristics.

Any suitable memory 416, 452 can be used for the respective components of the system 400. The memory 416 illustrates a type of computer-readable media, namely computer-readable storage media. Computer-readable storage media may include, but is not limited to, nonvolatile, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The user interface 456 of the external programming unit 406 can be, for example, a keyboard, mouse, touch screen, track ball, joystick, voice recognition system, or any combination thereof, and the like.

Figure 6:
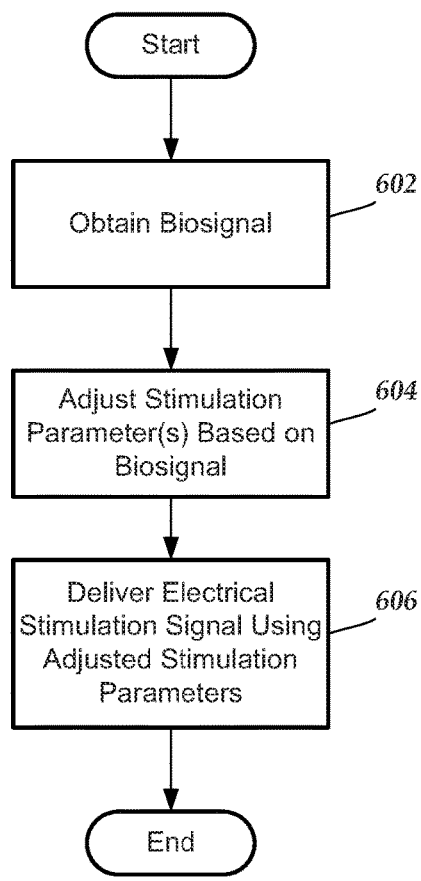
FIG. 6 is a flowchart of one embodiment of a method for adjusting stimulation parameters, according to the invention.

FIG. 6 is a flowchart of one embodiment of a method of adjusting stimulation parameters. In step 602, a biosignal is obtained. Examples of suitable biosignals include, but are not limited to, EEG, electrocochleograph (ECOG), heart rate, ECG, blood pressure, electrical signals traversing the spinal cord or a nerve or group of nerves, and the like. In some embodiments, more than one biosignal can be obtained or biosignals from two or more locations on the body of the patient can be obtained.

In step 604, one or more stimulation parameters are adjusted based on the obtained biosignal. Examples of stimulation parameters that can be adjusted include, but are not limited to, pulse frequency, pulse width, electrode selection (which may can also affect the location of stimulation), pulse amplitude, and the like. The size, intensity, and character of the stimulation may be controlled by adjusting the stimulation parameters (e.g., amplitude, frequency, impedance, voltage, pulse width, or the like) of the electrical stimulation signals. The adjustment can be manual or automatic. In at least some embodiments, the adjustment is part of a programming session and the adjustment may be performed using an external programming unit, a control module, or any other suitable device, or any combination thereof. In at least some embodiments, the adjustment is part of the operation of the electrical stimulation system outside of the programming session and may occur at a regular or irregular interval or when requested by a user or other individual. The adjustment may be performed using a control module or any other suitable device, or any combination thereof.

In step 606, an electrical stimulation signal is generated and delivered by the control module using the adjusted stimulation parameter or parameters.

Figure 7:
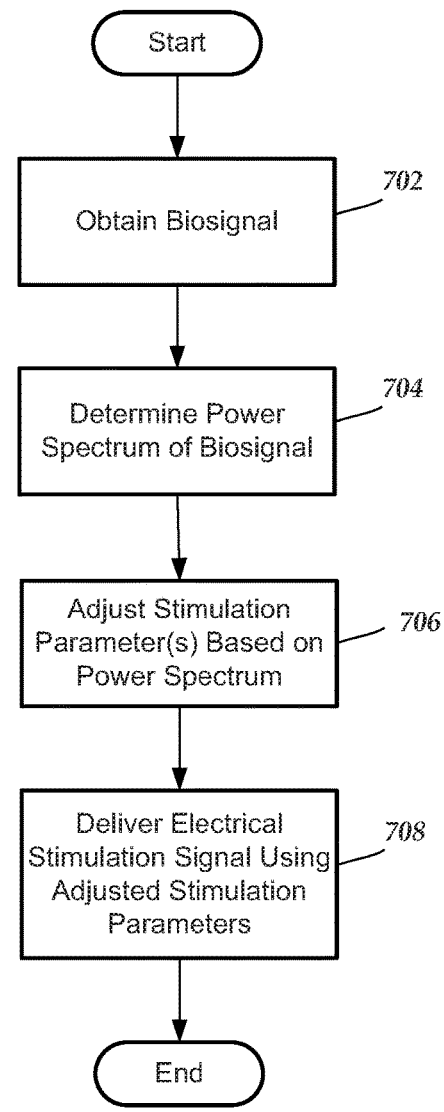
FIG. 7 is a flowchart of another embodiment of a method for adjusting stimulation parameters, according to the invention.

FIG. 7 is a flowchart of another embodiment of a method of adjusting stimulation parameters. In step 702, a biosignal is obtained and in step 704 a power spectrum of the biosignal is determined. The power spectrum may be determined by, for example, an external programming unit, a control module, or any other suitable device. In step 706, one or more stimulation parameters are adjusted based on the power spectrum. Examples of stimulation parameters that can be adjusted include, but are not limited to, pulse frequency, pulse width, electrode selection (which may can also affect the location of stimulation), pulse amplitude, and the like. The size, intensity, and character of the stimulation may be controlled by adjusting the stimulation parameters (e.g., amplitude, frequency, impedance, voltage, pulse width, or the like) of the electrical stimulation signals. The adjustment can be manual or automatic. In at least some embodiments, the adjustment is part of a programming session and the adjustment may be performed using an external programming unit, a control module, or any other suitable device, or any combination thereof. In at least some embodiments, the adjustment is part of the operation of the electrical stimulation system outside of the programming session and may occur at a regular or irregular interval or when requested by a user or other individual. The adjustment may be performed using a control module or any other suitable device, or any combination thereof. In step 708, an electrical stimulation signal is generated and delivered by the control module using the adjusted stimulation parameter or parameters.

Figure 8:
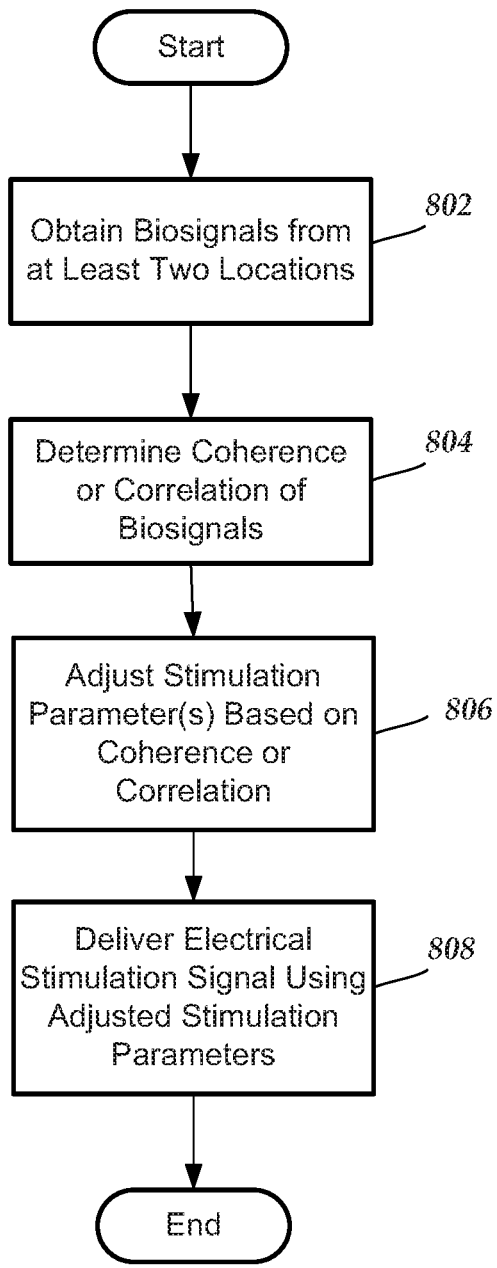
FIG. 8 is a flowchart of a further embodiment of a method for adjusting stimulation parameters, according to the invention.

FIG. 8 is a flowchart of another embodiment of a method of adjusting stimulation parameters. In step 802, two or more biosignals are obtained at different portion of the patient's body. In step 804, coherence, correlation, or other measure of association between the biosignals is determined. The coherence, correlation, or other measure of association may be determined by, for example, an external programming unit, a control module, or any other suitable device. In step 806, one or more stimulation parameters are adjusted based on the coherence, correlation, or other measure of association between the biosignals. Examples of stimulation parameters that can be adjusted include, but are not limited to, pulse frequency, pulse width, electrode selection (which may can also affect the location of stimulation), pulse amplitude, and the like. The size, intensity, and character of the stimulation may be controlled by adjusting the stimulation parameters (e.g., amplitude, frequency, impedance, voltage, pulse width, or the like) of the electrical stimulation signals. The adjustment can be manual or automatic. In at least some embodiments, the adjustment is part of a programming session and the adjustment may be performed using an external programming unit, a control module, or any other suitable device, or any combination thereof. In at least some embodiments, the adjustment is part of the operation of the electrical stimulation system outside of the programming session and may occur at a regular or irregular interval or when requested by a user or other individual. The adjustment may be performed using a control module or any other suitable device, or any combination thereof. In step 808, an electrical stimulation signal is generated and delivered by the control module using the adjusted stimulation parameter or parameters.

Figure 9:
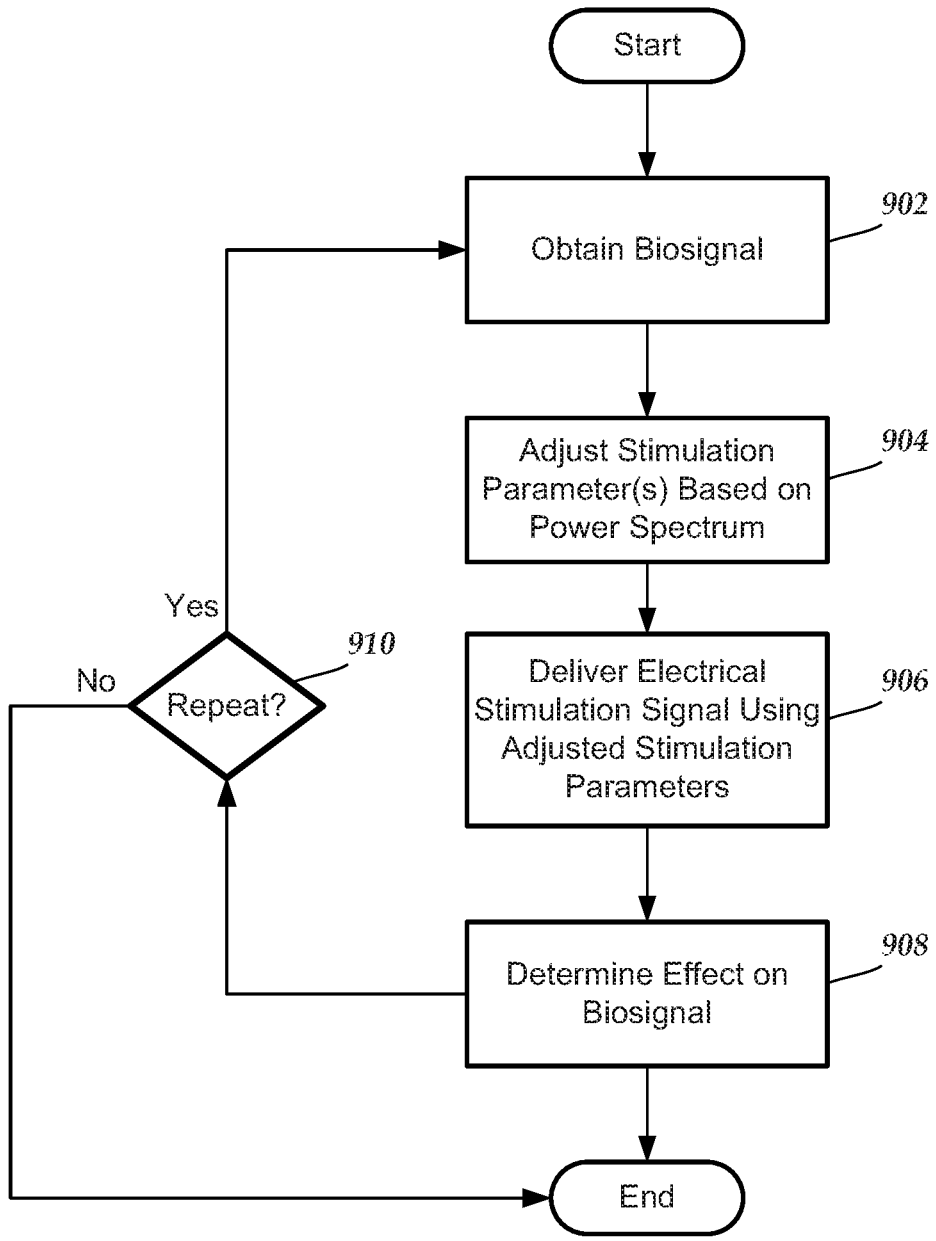
FIG. 9 is a flowchart of yet another embodiment of a method for adjusting stimulation parameters, according to the invention.

FIG. 9 is a flowchart of another embodiment of a method of adjusting stimulation parameters. In step 902, a biosignal is obtained. Optionally, a power spectrum can be determined from the biosignal, as described above with respect to the method illustrated in FIG. 7. Alternatively or additionally, two or more biosignals can be obtained and a coherence, correlation, or other measure of association between the biosignals can be determined, as described above with respect to the method illustrated in FIG. 8.

In step 904, one or more stimulation parameters are adjusted based on the power spectrum. Examples of stimulation parameters that can be adjusted include, but are not limited to, pulse frequency, pulse width, electrode selection (which may can also affect the location of stimulation), pulse amplitude, and the like. The size, intensity, and character of the stimulation may be controlled by adjusting the stimulation parameters (e.g., amplitude, frequency, impedance, voltage, pulse width, or the like) of the electrical stimulation signals. The adjustment can be manual or automatic. In at least some embodiments, the adjustment is part of a programming session and the adjustment may be performed using an external programming unit, a control module, or any other suitable device, or any combination thereof. In at least some embodiments, the adjustment is part of the operation of the electrical stimulation system outside of the programming session and may occur at a regular or irregular interval or when requested by a user or other individual. The adjustment may be performed using a control module or any other suitable device, or any combination thereof.

In step 906, an electrical stimulation signal is generated and delivered by the control module using the adjusted stimulation parameter or parameters. In step 908, the effect of the electrical stimulation signal can be determined. In at least some embodiments, the effect is determined by measuring a biosignal. In step 910, the system or a user can decide whether to repeat the procedure to further adjust the stimulation parameters. If the decision is to repeat, then steps 902-908 can be repeated as illustrate in FIG. 9. If the effect of the stimulation was determined using a biosignal that biosignal may be used in step 902.

This process can be used as a feedback loop to adjust stimulation parameters. The feedback loop may be part of a programming session. Alternatively or additionally, the electrical stimulation system may initiate the feedback loop on a regular or irregular basis or when requested by a user, clinician, or other individual to adjust stimulation parameters.

It will be understood that the system can include one or more of the methods described hereinabove with respect to FIGS. 6-9 in any combination. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks or described for the control modules, external programming units, sensors, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation system, comprising:
   an implantable control module configured and arranged for implantation in a body of a patient, wherein the control module is configured and arranged to provide electrical stimulation signals to an electrical stimulation lead coupled to the implantable control module for electrical stimulation of patient tissue, wherein the implantable control module comprises
   a processor configured and arranged to perform the following actions:
      obtaining at least two different biosignals of the patient,
      determining a measure of association between the at least two different biosignals,
      altering at least one stimulation parameter of the electrical stimulation system in response to the measure of association between the at least two different biosignals, and directing delivery of electrical stimulation signals to one or more selected electrodes of the electrical stimulation system using the at least one stimulation parameter.

2. The system of claim 1, wherein determining the measure of association comprises determining a measure of coherence between the at least two different biosignals.

3. The system of claim 1, wherein determining the measure of association comprises determining a measure of correlation between the at least two different biosignals.

4. The system of claim 1, wherein obtaining the at least two different biosignals of the patient comprises obtaining an electroencephalogram of a theta band for the patient and an electroencephalogram of a gamma band for the patient.

5. The system of claim 1, wherein obtaining the at least two different biosignals of the patient comprises obtaining a same type of biosignal at two different points in time.

6. The system of claim 1, wherein obtaining the at least two different biosignals of the patient comprises obtaining a same type of biosignal at two different locations on a body of the patient.

7. The system of claim 6, wherein directing delivery of the electrical stimulation signals comprises directing delivery of the electrical stimulation signals to a plurality of selected electrodes to produce stimulation to different stimulation sites.

8. The system of claim 1, wherein determining the measure of association comprises determining the measure of association between the at least two different biosignals to determine whether the measure of association is indicative of synchronous activity.

9. The system of claim 8, wherein directing delivery of the electrical stimulation signals comprises directing delivery of the electrical stimulation signals to a plurality of selected electrodes to produce stimulation to different stimulation sites to desynchronize the synchronous activity.

10. The system of claim 1, wherein determining the measure of association comprises determining the measure of association between the at least two different biosignals to determine whether the measure of association is indicative of pain.

11. An electrical stimulation system, comprising:
an implantable control module configured and arranged for implantation in a body of a patient and comprising an antenna and a processor coupled to the antenna, wherein the control module is configured and arranged to provide electrical stimulation signals to an electrical stimulation lead coupled to the implantable control module for electrical stimulation of patient tissue; and
an external programming unit configured and arranged to communicate with the processor of the implantable control module using the antenna and to adjust stimulation parameters for production of the electrical stimulation signals, wherein the external programming unit comprises a processor configured and arranged to perform the following actions:
obtaining at least two different biosignals of the patient,
determining a measure of association between the at least two different biosignals, and
altering at least one stimulation parameter of the electrical stimulation system in response to the measure of association between the at least two different biosignals;
wherein the processor of the implantable control module is configured to direct delivery of electrical stimulation signals to one or more selected electrodes of the electrical stimulation system using the at least one stimulation parameter.

12. The system of claim 11, wherein determining the measure of association comprises determining a measure of coherence between the at least two different biosignals.

13. The system of claim 11, wherein determining the measure of association comprises determining a measure of correlation between the at least two different biosignals.

14. The system of claim 11, wherein obtaining the at least two different biosignals of the patient comprises obtaining an electroencephalogram of a theta band for the patient and an electroencephalogram of a gamma band for the patient.

15. The system of claim 11, wherein obtaining the at least two different biosignals of the patient comprises obtaining a same type of biosignal at two different points in time.

16. The system of claim 11, wherein obtaining the at least two different biosignals of the patient comprises obtaining a same type of biosignal at two different locations on a body of the patient.

17. The system of claim 16, wherein directing delivery of the electrical stimulation signals comprises directing delivery of the electrical stimulation signals to a plurality of selected electrodes to produce stimulation to different stimulation sites.

18. The system of claim 11, wherein determining the measure of association comprises determining the measure of association between the at least two different biosignals to determine whether the measure of association is indicative of synchronous activity.

19. The system of claim 18, wherein directing delivery of the electrical stimulation signals comprises directing delivery of the electrical stimulation signals to a plurality of selected electrodes to produce stimulation to different stimulation sites to desynchronize the synchronous activity.

20. The system of claim 11, wherein determining the measure of association comprises determining the measure of association between the at least two different biosignals to determine whether the measure of association is indicative of pain.

* * * * *